United States Patent [19]

Youssefyeh et al.

[11] Patent Number: 4,619,944
[45] Date of Patent: Oct. 28, 1986

[54] ANTIHYPERTENSIVE COMPOUNDS

[75] Inventors: Raymond D. Youssefyeh, Tarrytown, N.Y.; Howard Jones, Holmdel, N.J.

[73] Assignee: USV Pharmaceutical Corporation, Fort Washington, Pa.

[21] Appl. No.: 703,054

[22] Filed: Feb. 19, 1985

Related U.S. Application Data

[62] Division of Ser. No. 269,166, Jun. 1, 1981, Pat. No. 4,507,136.

[51] Int. Cl.$^4$ .............. A61K 31/265; A61K 31/275; A61K 31/215; A61K 31/24
[52] U.S. Cl. .................... 514/513; 564/200; 549/450; 558/253; 549/72; 549/553; 558/4; 549/473; 546/315; 560/12; 546/291; 546/262; 564/154; 546/278; 548/343; 564/197; 548/527; 548/517; 564/198; 548/558; 544/159; 564/191; 544/396; 544/400; 544/131; 546/284; 562/430; 546/268; 546/306; 562/431; 546/309; 546/159; 562/556; 546/281; 546/271; 562/507; 544/128; 544/141; 514/528; 544/139; 514/521; 548/557; 548/336; 514/530; 548/327; 544/147; 514/531; 544/145; 544/121; 514/538; 544/374; 544/379; 514/539; 544/370; 514/541; 549/60; 549/59; 514/542; 514/562; 514/603; 514/605; 514/616; 514/618; 514/623; 514/624; 514/625; 514/626; 514/627; 514/629; 514/630
[58] Field of Search .............. 260/455 R; 560/9, 12; 564/154, 197, 198; 562/430, 431, 556, 507; 514/513, 528, 521, 530, 531, 538, 539, 541, 542, 562, 603, 605, 616, 618, 623, 624, 625, 626, 627, 629, 630; 558/1, 4

[56] References Cited

U.S. PATENT DOCUMENTS 4,256,761 3/1981 Suh et al. .............. 260/455 R

Primary Examiner—Henry R. Jiles
Assistant Examiner—Robert C. Whittenbaugh

[57] ABSTRACT

Provided are antihypertensive compounds of the formula

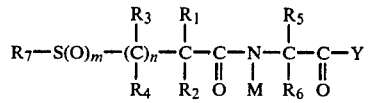

wherein
$R_1$, $R_2$, $R_3$, $R_4$, $R_5$, and $R_6$ are hydrogen, alkyl, alkenyl, alkynyl, phenyl-alkyl, or cycloalkyl, and may be the same or different,
m is an integer from 0 to 2 inclusive,
n is an integer from 0 to 4 inclusive,
M is alkenyl, alkynyl, cycloalkyl, cycloalkyl-alkyl, polycycloalkyl, polycycloalkyl-alkyl, aryl, aralkyl, heteroaryl, heteroaryl-alkyl, hetero-cycloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylaminoalkyl.
Y is hydroxy, alkoxy, amino, or substituted amino, aminoalkanoyl, aryloxy, aminoalkoxy, or hydroxyalkoxy, and
$R_7$ is alkyl, aryl, aralkyl, cycloalkyl, cycloalkyl-alkyl, heterocyclic, —CO—SR, —CS—SR,

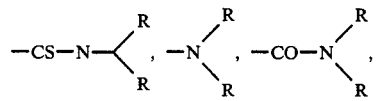

$CH_2CO_2R$, —CHM—$CO_2R$, —$CH_2$—CO—SR, —CN,

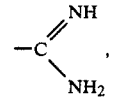

—CO—NH—$CH_2CO_2R$,

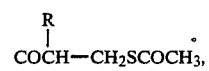

or —CO—$CO_2R$, wherein R is hydrogen, alkyl, or aryl, and where Y is hydroxy, their pharmaceutically acceptable, nontoxic alkali metal, alkaline earth metal, and amine salts.

12 Claims, No Drawings

ANTIHYPERTENSIVE COMPOUNDS

This application is a division of our copending application Ser. No. 269,166, filed June 1, 1981, now U.S. Pat. No. 4,507,136, issued Mar. 26, 1985.

This invention relates to new chemical compounds having valuable pharmaceutical activity. It particularly relates to amides having antihypertensive and angiotensin converting enzyme inhibitory activity of the structure

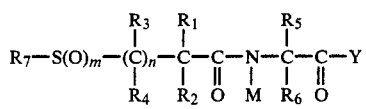

wherein $R_1$, $R_2$, $R_3$, $R_4$, $R_5$, and $R_6$ are hydrogen, alkyl, alkenyl, alkynyl, phenyl-alkyl, and cycloalkyl, and may be the same or different, m is an integer from 0 to 2 inclusive, n is an integer from 0 to 4 inclusive, M is alkenyl, alkynyl, cycloalkyl, cycloalkyl-alkyl, polycycloalkyl, polycycloalkyl-alkyl, aryl, aralkyl, heteroaryl, heteroaryl-alkyl, hetero-cycloalkyl, hetero-cycloalkyl-alkyl, fused aryl-cycloalkyl, fused aryl-cycloalkyl-alkyl, fused heteroaryl-cyloalkyl, fused heteroaryl-cycloalkyl-alkyl, alkoxyalkyl, alkylthioalkyl, alkylamino-alkyl, or dialkylaminoalkyl.

Y is hydroxy, alkoxy, amino, or substituted amino, aminoalkanoyl, aryloxy, aminoalkoxy, or hydroxyalkoxy, and $R_7$ is alkyl, aryl, aralkyl, cycloalkyl, cycloalkyl-alkyl, heterocyclic, —CO—SR, —CS—SR,

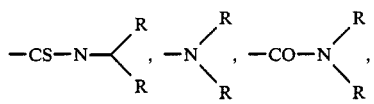

$CH_2CO_2R$, —CHM—$CO_2R$, —$CH_2$—CO—SR, —CN,

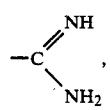

—CO—NH—$CH_2CO_2R$, or

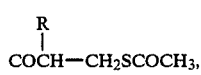

—CO—$CO_2R$, wherein R is hydrogen, alkyl, or aryl, and where Y is hydroxy, their pharmaceutically acceptable, nontoxic alkali metal, alkaline earth metal, and amine salts.

The alkyl groups per se and in the alkyl moiety in aralkyl, cycloalkyl-alkyl, polycycloalkyl-alkyl, heteroaryl-alkyl and the like, and, in alkoxy, alkylthio, alkanoyl, carbalkoxy, and alkylamino, may be straight-chained or branched and are preferably lower alkyl groups containing from 1 to 6 carbons. Such groups include methyl, ethyl, propyl, isopropyl, butyl, isobutyl, amyl, iso-amyl, hexyl, and the like.

The alkenyl and alkynyl groups may also be branched or straight-chained and contain from 2 to 6 carbon atoms. Such groups include vinyl, ethynyl, propenyl, allyl, isopropenyl, and the like.

The M cycloalkyl, polycycloalkyl, aryl, heteroaryl, arylalkyl, fused aryl-cycloalkyl groups and the like contain from 3 to 16 carbon atoms and may carry substituents such as lower alkyl, alkenyl, alkynyl, hydroxy, thio, amino, alkoxy, alkylthio, alkyl-amino, and halo. They include such radicals as cyclopropyl, cyclobutyl, cyclopentyl, cyclohexyl, cycloheptyl, adamantyl, norbornyl, phenyl, tolyl, benzyl, phenethyl, dimethoxyphenyl, hydroxybenzyl, indanyl, naphthyl, tetrahydronaphthyl, decahydronaphthyl, pyridyl, quinolyl, pyrrolidyl, pyrrolyl, morpholinyl, furyl, furfuryl, tetrahydrofurfuryl, benzimidazolyl, thienyl, imidazolyl, and the like.

The $R_7$ heterocyclic groups include the heterocyclic groups listed for M above as well as heterocyclic alkyl, and heterocyclic groups substituted with alkyl, alkenyl, alkynyl, hydroxy, hydroxyalkyl, alkoxy, halogen, thiol, alkylmercapto, amino, aminoalkyl, alkylamino, nitro, cyano, carboxy, carbalkoxy, carboxamido, sulfonyl, sulfonamido, trifluoromethyl, and methylenedioxy.

The aryl groups in M and $R_7$ aryl and aralkyl also include substituted aryl wherein the substituent is alkyl, alkenyl, alkynyl, hydroxy, hydroxyalkyl, alkoxy, halogen, thiol, alkylmercapto, amino, aminoalkyl, alkylamino, nitro, cyano, carboxy, carbalkoxy, carboxamido, sulfonyl, sulfonamido, trifluoromethyl and methylenedioxy.

The preferred compounds are those wherein M is cycloalkyl having 3 to 7 carbon atoms, $R_1$, $R_3$, $R_4$, $R_5$ and $R_6$ are hydrogen, $R_2$ is hydrogen or lower alkyl, preferably methyl, $R_7$ is COSR, $COCO_2R$, $CON(R)_2$, $CH_2CO_2R$, or $COCH(CH_3)CH_2SCOCH_3$, n is 0 or 1, and Y is hydroxy, wherein R is hydrogen, lower alkyl or phenyl.

The compounds of the present invention are prepared by the reaction of an appropriately substituted amino acid ester of the structure

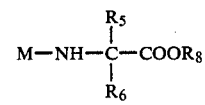

wherein $R_8$ is lower alkyl with a carboxylic acid of the structure (Compound 1)

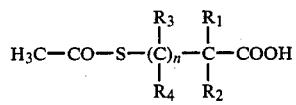

to produce an amide of the structure (Compound 2)

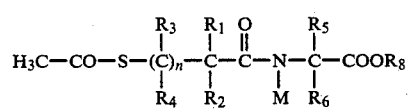

followed by hydrolysis of the acetyl group to yield the free thiol, providing a compound of the structure

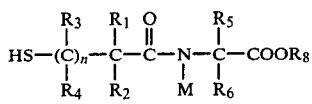

The hydrogen on the SH group can then be replaced by the desired $R_7$ group and the $R_8$ group can be replaced by a hydrogen atom by a subsequent hydrolysis step.

In place of compound II above, a compound of the structure (Compound III)

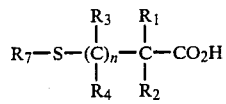

may be used, to give a compound having the desired $R_7$ substituents.

It is known to those skilled in the art that those amides of the present invention having an asymmetric carbon atom may exist in racemic or optically active levo or dextro forms. All of these forms are contemplated within the scope of this invention.

The invention will be more fully illustrated in the examples which follow. These examples are given by way of illustration and are not to be considered as limiting.

EXAMPLE 1

N(3-Phenylthio-2-methyl propanoyl)-N-cyclopentylglycine-t-butyl ester

To a cold solution of 19.9 g (0.1M) of N-cyclopentyl glycine-t-butyl ester in 200 ml THF was added 26 g dicyclohexyl carbodiimide. After stirring for ½ hour, a solution of 19.6 g (0.1M) of 3-phenylthio-2-methyl propanoic acid in 50 ml THF was added and stirring continued for 16 hours. It was then filtered, solvent removed, dissolved in ether, washed well with water, filtered, dried over MgSO₄, and evaporated to dryness leaving an oily residue which was purified by HPLC using ethyl acetate-hexane (3:17) as eluent.

EXAMPLE 2

N(3-Phenylthio-2-methyl propanoyl)-N-cyclopentyl glycine

To a cold solution of 7.5 g (0.02M) of N-(3-phenylthio-2-methyl propanoyl)-N-cyclopentyl glycine-t-butyl ester in 60 ml methylene chloride was slowly added a solution of 3 ml of trimethyl silyl iodide in 10 ml methylene chloride, stirring continued for 2 hours. Ice was added and the mixture extracted with 5% NaHCO₃. The aqueous solution was acidified with acetic acid, extracted with ethyl acetate, washed with water, dried over MgSO₄, and evaporated to dryness. The remaining oily residue was purified by HPLC using acetic acid-ethyl acetate-hexane (4:50:46) as eluent.

EXAMPLE 3

N-(3-Phenylsulfoxy-2-methylpropanoyl)-N-cyclopentyl glycine-t-butyl ester

A mixture of 5 g of N-(3-phenylthio-2-methyl propanoyl)-N-cyclopentyl glycine-t-butyl ester in 5 ml acetic acid and 3 ml of 30% hydrogen peroxide was stirred at room temperature for 2 hours. It was then diluted with water and extracted with ethyl acetate. The organic layer was washed with water, dried over MgSO₄ and evaporated to dryness leaving 2.9 g oily residue which was purified by HPLC using 30% ethyl acetate-hexane as eluent giving pure colorless oily product.

EXAMPLE 4

N-(3-Phenylsulfoxy-2-methylpropanoyl)-N-cyclopentyl-glycine

A mixture of 1.6 g of N-(3-phenylthio-2-methyl propanoyl)-N-cyclopentyl glycine in 5 ml acetic acid and one ml of 30% hydrogen peroxide was stirred at room temperature for 2 hours. It was then diluted with water and extracted with ethylacetate. The organic layer was washed with water, dried over MgSO₄ and evaporated to dryness. The remaining oily residue was crystallized from ether-hexane, m.p. 135°–7° C.

EXAMPLE 5

N-(3-Phenylsulfonyl-2-methyl propanoyl)-N-cyclopentylglycine-t-butyl ester

A mixture of 12 g of N-(3-phenylthio-2-methyl propanoyl)-N-cyclopentylglycine-t-butyl ester in 10 ml acetic acid and 10 ml 30% hydrogen peroxide was stirred at room temperature for 48 hours. It was then diluted with water and extracted with ethylacetate. The organic layer was washed with H₂O, dried over MgSO₄, and evaporated to dryness. The crude oily residue was purified by HPLC using 40% EtOAc-hexane.

EXAMPLE 6

N-[3-(3-Acetylthio-2-methylpropanoyl thio)-2-methyl-propanoyl]-N-cyclopentyl glycine-t-butyl ester To a mixture of 3 g (0.01M) of N-(3-mercapto-2-methyl propanoyl)-N-cyclopentyl glycine-t-butyl ester, 1.2 g (0.012M) triethylamine in 100 ml methylene chloride was added a solution of 1.8 g (0.01M) of 3-acetylthio-2-methyl propanoyl chloride and stirring continued for 8 hours. It was then washed with water, dried over MgSO₄ and evaporated to dryness leaving an oily residue which was purified by HPLC using ethyl acetate-hexane (1:3) as eluent.

EXAMPLE 7

N-[3-(3-Acetylthio-2-methylpropanoylthio)-2-methyl propanoyl)]-N-cyclopentyl glycine To a cold solution of 4.5 g (0.01) of N-[3-(3-acetylthio-2-methylpropanoylthio)-2-methyl propanoyl]-N-cyclopentyl glycine-t-butyl ester in 50 ml methylene chloride was added 2.2 g (0.011M) trimethylsilyl iodide in 10 ml methylene chloride and stirring continued for 2 hours. Ice was then added and extracted with 5% NaHCO₃. The basic solution was acidified with acetic acid, extracted with ethylacetate, dried over MgSO₄ and evaporated to dryness. The oily residue was purified by HPLC using HOAc-EtOAc-hexane (4:46:50) as eluent.

EXAMPLE 8

N-(3-Phenylcarbamoylthio-2-methyl-propanoyl)-N-cyclopentyl glycine

A mixture of 4.9 g (0.02M) of N-(3-mercapto-2-methyl propanoyl)-N-cyclopentyl glycine and 8 ml of phenyl isocyanate in 5 ml methylene chloride was stirred at room temperature for 72 hours. The mixture was diluted with ether and filtered. The ether solution was washed with water, dried over MgSO$_4$ and evaporated to dryness. The crude residue was dissolved in acetonitrile, treated with charcoal and crystallized by addition of ether, m.p. 170°–172° C.

EXAMPLE 9

N-[3-(N'-Carbethoxymethylcarbamoylthio)-2-methyl propanoyl]-N-cyclopentyl glycine-t-butyl-ester A mixture of 5 g of N-(3-mercapto-2-methyl propanoyl)-N-cyclopentyl glycine-t-butyl ester and 6 ml of ethyl isocyanotoacetate was stirred at 80° C. for 48 hours. The mixture was cooled, stirred with water and filtered. The aqueous layer was extracted with ether. The ether extract was washed with water, dried over MgSO$_4$ and evaporated to dryness. The oily residue was purified by HPLC using EtOAc-hexane (3:17) as eluent.

EXAMPLE 10

N-[3-(N'-Carbethoxymethylcarbamoylthio)-2-methyl-propanoyl]-N-cyclopentyl glycine To an ice-cold solution of 2.9 g (7 mmol) of N-[3-(N'-carbethoxymethylcarbamoylthio)-2-methyl propanoyl]-N-cyclopentyl glycine-t-butyl ester in 25 ml methylene chloride was slowly added 1 ml (7.5 mmol) of trimethylsilyl iodide in 5 ml methylene chloride and stirring continued for 2 more hours. Ice was added and extracted with 5% NaHCO$_3$ solution. The base extract was acidified with acetic acid and extracted with ethyl acetate which was dried over MgSO$_4$ and evaporated to dryness. The remaining oily residue 1.5 g was purified by HPLC using HOAc-EtOAc-hexane (4:46:50) as eluent.

EXAMPLE 11

N-(3-Ethylthio-2-methylpropanoyl)-N-cyclopentyl glycine-ethyl ester

To a solution of 0.45 g (0.02M) of sodium in 50 ml ethanol was dropwise added a solution of 4.8 g of N-(3-mercapto-2-methyl propanoyl)-N-cyclopentyl glycine ethyl ester in 10 ml ethanol and stirring continued for 1 hour. Then, 3.04 g (0.02M) ethyl iodide in 5 ml ethanol was added and stirring continued for 4 hours. The solution was concentrated in vacuum, diluted with ether, washed with water, dried over MgSO$_4$ and evaporated to dryness. The oily residue was chromatographed by HPLC using EtOAc-hexane (3:17) as eluent.

EXAMPLE 12

N-(3-Ethylthio-2-methyl-propanoyl)-N-cyclopentyl-glycine

A mixture of 3.8 g (0.012) of N-(3-ethylthio-2-methyl propanoyl)-N-cyclopentyl glycine ethyl ester in 80 ml of 10% NaOH was stirred for 7 hours. It was then cooled, acidified with 10% HCl, extracted with ether, dried over MgSO$_4$, and evaporated to dryness giving oily residue which was purified by HPLC using HOAc-EtOAc-Hexane (5:45:50).

EXAMPLE 13

N-(3-Thioethylformatethio-2-methyl-propanoyl-N-cyclopentyl glycine-t-butyl ester To a solution of 3 g (0.01) of N-(3-mercapto-2-methyl propanoyl)-N-cyclopentyl glycine-t-butyl ester and 3 ml triethylamine in 50 ml ether was added 1.5 g (0.012) ethyl chlorothioformate in 10 ml ether, stirring continued for 16 hours. It was then washed with water, dried and evaporated leaving oily residue which crystallized on standing. Recrystallization from ether-hexane, m.p. 106°–108° C.

EXAMPLE 14

N-(3-Thioethylformatethio-2-methyl-propanoyl)-N-cyclopentyl glycine

To a cold mixture of 2.6 g (0.007) of N-(3-thioethylformatethio-2-methyl propanoyl)-N-cyclopentyl glycine-t-butyl ester in 50 ml CH$_2$Cl$_2$ was added a solution of 1 ml (0.0075) of trimethylsilyl iodide in 10 ml CH$_2$Cl$_2$, stirring continued for 2 hours. Ice was added, extracted with 5% NaHCO$_3$, acidified with HOAc, extracted with EtOAc, washed with H$_2$O, dried over MgSO$_4$ and evaporated to dryness. The oily residue was purified by HPLC using HOAc-hexane-EtOAc (3:48:50), m.p. 83°–85° C.

EXAMPLE 15

N-(3-Ethyloxalylthio-2-methyl-propanoyl)-N-cyclopentyl-glycine t-butyl ester

To a mixture of 9 g (0.03) of N-(3-mercapto-2-methyl propanoyl)-N-cyclopentyl glycine-t-butyl ester, 5 ml Et$_3$N in 150 ml ether was added 5 g (0.035) of ethyl chloro oxalate in 10 ml ether. Stirred at room temperature for 6 hours, 200 ml ether was added, washed with water, 3% HCl, water saturated with NaHCO$_3$, water dried over MgSO$_4$, evaporated to dryness leaving an oily residue which was purified by HPLC using 20% EtOAc-hexane, m.p. 67°–70° C.

EXAMPLE 16

N-(3-Ethyloxalylthio-2-methyl propanoyl)-N-cyclopentyl glycine

To a cold mixture of 3 g of N-(3-ethyloxalylthio-2-methyl propanoyl)-N-cyclopentyl glycine-t-butyl ester in 50 ml methylene chloride was added 1 ml of trimethyl silyl iodide in 10 ml methylene chloride. Stirring continued for 2 hours. Ice was then added, extracted with 5% NaHCO$_3$ solution, acidified with acetic acid and extracted with ethylacetate. The extract was washed with water, dried over MgSO$_4$ and evaporated to dryness. The oily residue was purified by HPLC using HOAc-EtOAc-hexane (4:46:50).

EXAMPLE 17

N-(3-Thiosulfate-2-methyl propanoyl)-N-cyclopentyl glycine-t-butyl ester

To a cold solution of 1.8 g of N-(3-mercapto-2-methyl propanoyl)-N-cyclopentyl glycine-t-butyl ester, 2.5 triethylamine in 10 ml methylene chloride was slowly added 1.4 ml chlorosulfonic acid in 5 ml methylene chloride, stirring continued at room temperature overnight. It was diluted with water and extracted with methylene chloride. The organic layer was dried over MgSO$_4$ and evaporated to dryness to give the product.

EXAMPLE 18

N(3-Thiocyano-2-methyl-Propanoyl)-N-cyclopentyl-glycine-t-butyl ester

A mixture of 2 g of N(3-bromo-2-methyl-propanoyl)-N-cyclopentyl glycine-t-butyl ester, 0.7 g potassium thiocyanide in 5 ml water and 40 ml ethanol was stirred and refluxed for 16 hours. After removal of the solvent, it was diluted with water and extracted with ethyl acetate. The organic layer was dried over MgSO$_4$ and evaporated to dryness. The oily residue was purified by HPLC using 20% EtOAc-hexane as eluent giving pure N(3-thiocyano-2-methyl propanoyl)-N-cyclopentyl glycine-t-butyl ester.

EXAMPLE 19

N-(2-Thiocyano-propanoyl)-N-(Cyclopentyl)-glycine-t-butyl ester

A mixture of 1.5 g of N-(2-bromo-propanoyl)-N-cyclopentyl glycinet-butyl ester, 0.7 g potassium thiocyanide in 5 ml water and 24 ml ethanol was refluxed for 16 hours. After removal of the solvent, it was diluted with water and extracted with ether. The ether layer was dried over MgSO$_4$ and evaporated to dryness. The crude product was crystallized from ether-hexane giving 0.9 g pure N(2-thiocyano-propanoyl)-N-cyclopentyl glycine-t-butyl ester, m.p. 76°–78° C.

By following the procedures described above, the following additional compounds in which Y is hydroxy, n is 1, $R_1$, $R_3$, $R_4$, $R_5$ and $R_6$ are hydrogen, $R_2$ is hydrogen or lower alkyl and M is cyclopentyl, can be prepared:

| $R_2$ | $R_7$ |
|---|---|
| CH$_3$ | furoyl |
| CH$_3$ | thiofuroyl |
| H | nicotinoyl |
| CH$_3$ | isonicotinoyl |
| CH$_3$ | 2-thioketocyclopentylcarbonyl |
| H | 2-thioketocyclohexylcarbonyl |
| CH$_3$ | 2-imidazolylcarbonyl |
| CH$_3$ | H$_5$C$_2$OCH$_2$CHOHCH$_2$— |
| CH$_3$ | (H$_3$C)$_2$NCH$_2$CHOHCH$_2$— |
| H | CH$_3$CH(SH)CH$_2$— |
| CH$_3$ | 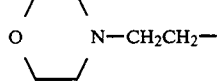 |
| CH$_3$ | (H$_5$C$_2$)$_2$NCH$_2$CH$_2$— |
| CH$_3$ | 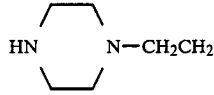 |
| H | 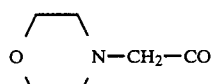 |
| CH$_3$ | 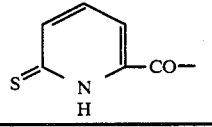 |
| CH$_3$ | 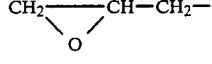 |

The compounds of the present invention have demonstrated potent activity (of the other of I$_{50}$ of 0.01 to 0.05 micromols) in the angiotensin converting enzyme (ACEI activity) when tested by the method described in Science 196, 441–4 (1977). As such, these compounds would be very useful in the treatment of hypertension. The compounds may be administered orally or parenterally in the treatment of hypertension in animals, and it will be within the skill of the practitioner to determine the exact amount to be administered and the mode of administration.

We claim:

1. Compounds of the formula

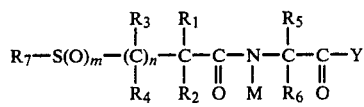

wherein $R_1$, $R_2$, $R_3$, $R_4$, $R_5$, and $R_6$ are hydrogen, $C_1$–$C_6$ alkyl, $C_2$–$C_6$ alkenyl, $C_2$–$C_6$ alkynyl, phenyl-$C_1$–$C_6$-alkyl, or $C_3$–$C_{16}$ cycloalkyl, and may be the same or different, m is an integer from 0 to 2 inclusive, n is an integer from 0 to 4 inclusive, M is $C_2$–$C_6$ alkenyl, $C_2$–$C_6$ alkynyl, $C_3$–$C_{16}$ cycloalkyl, $C_3$–$C_{16}$ cycloalkyl-$C_1$–$C_6$ alkyl, $C_3$–$C_{16}$ polycycloalkyl, $C_3$–$C_{16}$ polycycloalkyl-$C_1$–$C_6$ alkyl, $C_1$–$C_6$-alkoxy-$C_1$–$C_6$-alkyl, $C_1$–$C_6$-alkylthio-$C_1$–$C_6$-alkyl, $C_1$–$C_6$-alkylamino-$C_1$–$C_6$-alkyl, di-$C_1$–$C_6$-alkylamino-$C_1$–$C_6$-alkyl, phenyl, phen-$C_1$–$C_6$-alkyl, Y is hydroxy, $C_1$–$C_6$ alkoxy, amino, amino-$C_1$–$C_6$-alkanoyl, phenoxy, amino-$C_1$–$C_6$-alkoxy, or hydroxy-$C_1$–$C_6$-alkoxy, and $R_7$ is alkyl, phenyl, phen-$C_1$–$C_6$-alkyl, $C_3$–$C_{16}$-cycloalkyl, $C_3$–$C_{16}$-cycloalkyl-$C_1$–$C_6$-alkyl,

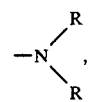

CH$_2$CO$_2$R, —CHM—CO$_2$R, —CH$_2$—CO—SR, —CN,

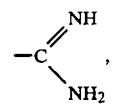

—CO—NH—CH$_2$CO$_2$R, or

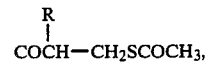

wherein R is hydrogen, $C_1$–$C_6$ alkyl, or phenyl and where Y is hydroxy, their pharmaceutically acceptable, nontoxic alkali metal, alkaline earth metal, and amine salts provided that if $R_7$ is —CN or

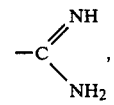

then m is not zero.

2. Compounds of the formula

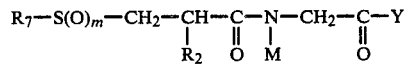

wherein

Y is hydroxy or lower alkoxy, $R_2$ is hydrogen or lower alkyl,

M is cycloalkyl having 3 to 7 carbon atoms, m is 0 to 2, and $R_7$ is $CH_2CO_2R$, or $COCH(CH_3)CH_2SCOCH_3$, wherein R is hydrogen, lower alkyl, or phenyl.

3. A compound according to claim 2 wherein M is cyclopentyl.

4. A compound according to claim 3 wherein Y is hydroxy.

5. A compound according to claim 4 wherein m is 0.

6. A compound according to claim 5 wherein $R_2$ is hydrogen.

7. A compound according to claim 6 wherein $R_7$ is $-CH_2CO_2H$.

8. A compound according to claim 6 wherein $R_7$ is $COCH(CH_3)CH_2SCOCH_3$.

9. A method of treating hypertension which comprises administering to the hypertensive animal an effective amount of a compound according to claim 1.

10. A compound according to claim 3 wherein m is 0, and $R_7$ is $-CH_2CO_2C_2H_5$.

11. Compounds of the formula

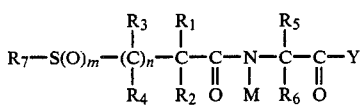

wherein $R_1$, $R_2$, $R_3$, $R_4$, $R_5$, and $R_6$ are hydrogen, $C_1$-$C_6$ alkyl, $C_2$-$C_6$ alkenyl, $C_2$-$C_6$ alkynyl, phenyl-$C_1$-$C_6$-alkyl, or $C_3$-$C_{16}$ cycloalkyl, and may be the same or different, m is an integer from 0 to 2 inclusive, n is an integer from 0 to 4 inclusive, M is $C_1$-$C_6$-alkoxy-$C_1$-$C_6$-alkyl, cyclo-$C_1$-$C_7$-alkyl or indanyl, Y is hydroxy, $C_1$-$C_6$ alkoxy, amino, amino-$C_1$-$C_6$-alkanoyl, phenoxy, amino-$C_1$-$C_6$-alkoxy, or hydroxy-$C_1$-$C_6$-alkoxy, and $R_7$ is $C_1$-$C_6$ alkyl, phenyl, phen-$C_1$-$C_6$-alkyl, $C_3$-$C_{16}$ cycloalkyl, $C_3$-$C_{16}$-cycloalkyl-$C_1$-$C_6$-alkyl, $-CO-SR$, $-CS-SR$,

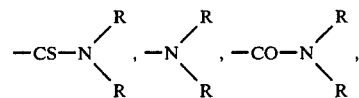

$CH_2CO_2R$, $-CHM-CO_2R$, $-CH_2-CO-SR$, $-CN$,

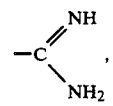

$-CO-NH-CH_2CO_2R$,

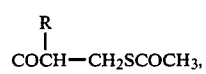

or $-CO-CO_2R$, wherein R is hydrogen, or $C_1$-$C_6$ alkyl, and where Y is hydroxy, their pharmaceutically acceptable, nontoxic alkali metal, alkaline earth metal, and amine salts, provided that when m is zero then $R_7$ is not $-CO-SH$, $-CO-S-(C_1$-$C_6$-alkyl), $-CN$, or

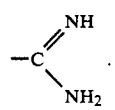

12. A method of treating hypertension which comprises administering to the hypertensive animal an effective amount of a compound according to claim 11.

* * * * *